United States Patent [19]

Carel et al.

[11] 4,143,081
[45] Mar. 6, 1979

[54] PREVENTION OF COLOR DETERIORATION OF DIPHENYLALKANES

[75] Inventors: Alfred B. Carel; Jerry W. Wimberley, both of Ponca City, Okla.

[73] Assignee: Continental Oil Company, Ponca City, Okla.

[21] Appl. No.: 899,917

[22] Filed: Apr. 26, 1978

[51] Int. Cl.$^2$ .............................................. C07C 7/18
[52] U.S. Cl. ................................ 260/666.5; 252/397; 252/401
[58] Field of Search ..................... 260/666.5; 252/397, 252/401

[56] References Cited

U.S. PATENT DOCUMENTS

| | | | |
|---|---|---|---|
| 2,355,993 | 8/1944 | Morgan | 252/59 |
| 2,398,468 | 4/1946 | Schultze et al. | 260/666.5 |
| 2,980,599 | 4/1961 | Morse | 260/666.5 |
| 3,377,315 | 4/1968 | Ashton et al. | 260/666.5 |
| 3,673,093 | 6/1972 | Rocchi | 260/666.5 |

FOREIGN PATENT DOCUMENTS 916553  1/1963  United Kingdom ................. 260/666.5

Primary Examiner—C. Davis
Attorney, Agent, or Firm—Bayless E. Rutherford, Jr.

[57] ABSTRACT

A method of preventing, or substantially reducing, the amount of color deterioration of diphenylalkanes, said diphenylalkanes being in contact with a color-deteriorating material, is disclosed. Briefly, the method comprises contacting the diphenylalkanes with an effective amount of ammonia or certain amines.

10 Claims, No Drawings

PREVENTION OF COLOR DETERIORATION OF DIPHENYLALKANES

GENERAL BACKGROUND

Diphenylalkanes are useful materials of commerce in that they are used as secondary plasticizers. In order to be used it is necessary that they have very little color. Typically, the material of commerce will have a light yellow or yellow color. Unfortunately, under some conditions, the product turns to a green color which renders it unsuitable for use as a secondary plasticizer.

We have found a method of preventing, or substantially reducing, this color deterioration of diphenylalkanes. Briefly, the method comprises contacting the diphenylalkanes with an effective amount of ammonia or certain amines.

BRIEF SUMMARY OF THE INVENTION

Briefly stated, the present invention is directed to a method of preventing, or substantially reducing, the amount of color deterioration of diphenylalkanes, said diphenylalkanes being in contact with a color-deteriorating material, said method comprising contacting the diphenylalkanes with an effective amount of ammonia or certain amines.

DETAILED DESCRIPTION

Suitable diphenylalkanes for use in our invention can be represented by the formula

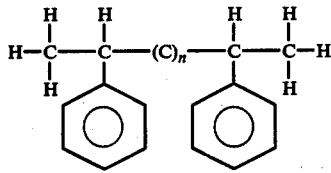

wherein n is an integer of from 2 to 14 preferably 6 to 10 and wherein the phenyl groups are attached to any carbon other than the terminal carbon atom.

Hydrocarbon compositions containing about 50 weight percent or higher diphenylalkanes and wherein the remaining hydrocarbons have a boiling range similar to the diphenylalkanes, are also suitable.

An example of a suitable hydrocarbon composition containing diphenylalkanes is a distillate by-product fraction from the preparation of mono-n-alkylbenzenes, such as disclosed by U.S. Pat. No. 3,316,294.

Briefly, U.S. Pat. No 3,316,294 relates to a process of preparing a detergent alkylate, wherein the process comprises the following steps, broadly stated: (a) separating a fraction of substantially straight-chain $C_8$–$C_{18}$ hydrocarbons from a petroleum distillate substantially free of olefins and containing said straight-chain hydrocarbons together with non-straight chain hydrocarbons, (b) chlorinating said fraction to the extent whereby between about 10 and about 35 mole percent of the straight-chain hydrocarbons present are substantially only mono-chlorinated, (c) alkylating an aromatic compound, e.g. benzene, with the chlorination product of step (b) in the presence of an alkylation catalyst, and (d) recovering from the reaction mass, by distillation, a fraction consisting essentially of mono-n-alkylbenzenes.

The diphenylalkane fraction is the fraction distilling after the mono-n-alkylbenzenes. Typically, the diphenylalkane fraction has a boiling range of about 326° to about 400° C. at 760 mm. Hg. pressure. It contains about 50 weight percent diphenylalkanes, wherein the alkyl chain contains from 10 to 14 carbon atoms. Additionally, it contains about 35 weight percent mono-n-alkylbenzenes and 10 to 15 weight percent di-n-alkylbenzenes. The product can contain up to about 5 weight percent of miscellaneous hydrocarbons.

The diphenylalkanes normally have a color ranging from light yellow to yellow. Exposure to certain conditions causes the material to turn to dark green color rendering it unsuitable for use as a secondary plasticizer. For example, storage in an iron vessel causes color deterioration.

We have found that contacting the diphenylalkanes with an effective amount of ammonia or certain amines prevents, or substantially reduces, the color deterioration of the diphenylalkanes. By contacting we mean admixing with the ammonia or amines; also, in the case of ammonia, we mean maintaining a blanket or covering over the diphenylalkanes in the storage vessel.

Suitable amines for use in our process include primary, secondary and tertiary amines which have the following properties: (1) soluble in the diphenylalkanes and (2) have a boiling range similar to the diphenylalkanes. (The term diphenylalkanes as used herein refers to diphenylalkanes per se and to hydrocarbon compositions containing diphenylalkanes as described in the foregoing). Preferred amines are tertiary amines, such as triheptylamine, trioctylamine, trinonylamine, and triethanolamine.

A suitable amount of ammonia or amine is in the range of about 0.0005 to about 2 weight percent based on the diphenylalkanes. A preferred amount is in the range of about 0.05 to about 1 weight percent on the same basis.

The temperature and pressure under which the contacting is done are not important. Ambient conditions are usually employed.

In order to illustrate the nature of the present invention still more clearly the following examples will be given. It is to be understood, however, that the invention is not to be limited to the specific conditions or details set forth in these examples except insofar as such limitations are specified in the appended claims.

The diphenylalkane used in all examples was a by-product of the manufacture of $C_{10}$–$C_{14}$-n-alkylbenzenes. The material had the composition described in the foregoing.

EXAMPLE 1

One hundred gram portions of the diphenylalkane were treated as shown in the following table. The results obtained (i.e. color effect) are shown also in the table.

| | | | Absorbance* | |
|---|---|---|---|---|
| Sample | Materials Added | | 8 days | 60 days |
| 1 | None | | <0.08 | 0.25 |
| 2 | Fe 1g | NH$_3$ Vapor Contacted | <0.08 | 0.08 |
| 3 | | NH$_3$ Vapor Contacted | <0.08 | — |
| 4 | Fe 1g | HCl 0.35g | >0.23 | — |
| 5 | Fe 1g | Triethanolamine 0.5g | <0.08 | — |
| 6 | Fe 1g | Trioctylamine 0.5g | <0.08 | — |
| 7 | | Triethanolamine 0.5g | <0.08 | — |
| 8 | | Trioctylamine 0.5g | <0.08 | — |
| 9 | FeCl$_3$ 0.5g | | >0.23 | — |

*At 616 millimicrons using 1 cm cells. This is wavelength where maximum green color was found.

The preceding data shows that the addition of ammonia and the specified amines reduced the green color which results on color deterioration of diphenylalkanes.

Additionally, it should be noted that all samples having an absorbance of 0.08 or less were a yellow to light yellow color.

Thus, having described the invention in detail, it will be understood by those skilled in the art that certain variations and modifications may be made without departing from the spirit and scope of the invention as defined herein and in the appended claims.

We claim:

1. A method of preventing, or substantially reducing, the color deterioration of diphenylalkanes, said diphenylalkanes being in contact with a color-deteriorating material, said method comprising contacting said diphenylalkanes with an effective amount, in the range of about 0.0005 to about 2 weight percent, based on the diphenylalkanes, of ammonia or a primary, secondary or tertiary amine, said amine having the following properties (a) soluble in the diphenylalkanes and (b) having a boiling range similar to said diphenylalkanes, said method being characterized further in that the term diphenylalkanes refers to (a) a material represented by the formula

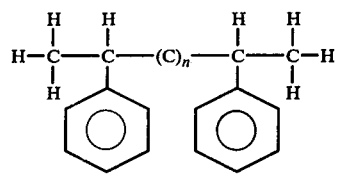

wherein n is an integer of from 2 to 14 and wherein the phenyl groups are attached to any carbon other than the terminal carbon atom and (b) hydrocarbon composition containing at least about 50 weight percent diphenylalkanes and wherein the remaining hydrocarbons have a boiling range similar to the diphenylalkanes.

2. The method of claim 1 wherein the diphenylalkanes are contacted with ammonia.

3. The method of claim 1 wherein the diphenylalkanes are contacted with triethanolamine.

4. The method of claim 1 wherein the diphenylalkanes are contacted with trioctylamine.

5. The method of claim 1 wherein the diphenylalkanes are present in a hydrocarbon composition containing at least 50 weight percent diphenylalkanes and wherein the remaining hydrocarbons have a boiling range similar to the diphenylalkanes.

6. The method of claim 5 wherein the alkyl chain of said diphenylalkanes contain 10 to 14 carbon atoms.

7. The method of claim 6 wherein the amount of ammonia or amine is in the range of about 0.05 to about 1 weight percent.

8. The method of claim 7 wherein the diphenylalkanes are contacted with ammonia.

9. The method of claim 7 wherein the diphenylalkanes are contacted with triethanolamine.

10. The method of claim 7 wherein the diphenylalkanes are contacted with trioctylamine.

* * * * *